(12) United States Patent
Podolsky et al.

(10) Patent No.: US 11,109,982 B2
(45) Date of Patent: Sep. 7, 2021

(54) SYSTEM AND METHOD FOR TOTAL HIP ARTHROPLASTY

(71) Applicant: iHip Surgical, LLC, Fountain Valley, CA (US)

(72) Inventors: Anatol Podolsky, Fountain Valley, CA (US); Yuri Garbuzov, Fountain Valley, CA (US)

(73) Assignee: iHip Surgical, LLC, Fountain Valley, CA (US)

( * ) Notice: Subject to any disclaimer, the term of this patent is extended or adjusted under 35 U.S.C. 154(b) by 0 days.

(21) Appl. No.: 17/014,362

(22) Filed: Sep. 8, 2020

(65) Prior Publication Data

US 2021/0068979 A1    Mar. 11, 2021

Related U.S. Application Data

(60) Provisional application No. 62/897,302, filed on Sep. 7, 2019.

(51) Int. Cl.
*A61F 2/46* (2006.01)
*A61B 17/17* (2006.01)

(52) U.S. Cl.
CPC ........ *A61F 2/4609* (2013.01); *A61B 17/1746* (2013.01); *A61F 2/4607* (2013.01); *A61F 2/4684* (2013.01)

(58) Field of Classification Search
CPC ............ A61B 17/1742; A61B 17/1746; A61B 17/175; A61F 2/3601
See application file for complete search history.

(56) References Cited

U.S. PATENT DOCUMENTS

| | | | | |
|---|---|---|---|---|
| 5,880,976 | A * | 3/1999 | DiGioia, III | A61B 17/155 703/7 |
| 5,995,738 | A * | 11/1999 | DiGioia, III | A61B 17/155 703/11 |
| 10,206,695 | B2 * | 2/2019 | Meridew | A61B 34/10 |
| 2015/0088146 | A1 * | 3/2015 | McCarthy | A61B 17/1666 606/91 |
| 2016/0030199 | A1 * | 2/2016 | Hunt | A61F 2/4684 623/23.42 |
| 2016/0030200 | A1 * | 2/2016 | Hunt | A61F 2/3662 623/20.35 |

* cited by examiner

*Primary Examiner* — Anu Ramana
(74) *Attorney, Agent, or Firm* — Crockett & Crockett, PC; K. David Crockett, Esq.

(57) ABSTRACT

Systems and methods for placement of both the prosthetic acetabular cup and the prosthetic femoral head which takes account of the patient's particular anatomy, with interoperative testing of the patient's body to find an optimum positioning (angles) for the components. The system allows a procedure with less pre-operative and inter-operative imaging, providing for reduced radiation exposure for doctors and patients.

13 Claims, 6 Drawing Sheets

SYSTEM AND METHOD FOR TOTAL HIP ARTHROPLASTY

This application claims priority to U.S. Provisional Application 62/897,302, filed Sep. 7, 2019.

FIELD OF THE INVENTIONS

The inventions described below relate to the field of total hip arthroplasty (hip replacement surgery).

BACKGROUND OF THE INVENTIONS

Total hip replacement entails replacement of the natural hip socket (the acetabulum) and the natural ball of the femoral head with a prosthetic cup installed in the pelvis, and a prosthetic ball. Dislocation of the prosthetic replacement ball from the replacement cup is a common complication of hip replacement surgery, and may be caused by poor alignment of the replacement parts with the patient's anatomy. Standard alignment for patients with healthy backs, for example, may be unsuitable for patients with an inflexible lower back, because certain motions such as sitting may result in dislocation unless the prostheses are aligned to account for stresses imposed on the prosthetic joint.

Current recommendations for placement of the acetabular cup position include positioning the acetabular cup at a tilt angle (abduction angle) of 40°±10° from the horizontal, and an anteversion angle of 15°±10°. The tilt angle (abduction angle) is the angle that the rim of the prosthetic acetabular cup is tilted upward and outward, such that its central axis is tilted away from the patient's superior/inferior axis and upward relative to the patient's horizontal axis (the transverse or axial plane) within a plane parallel to the coronal plane (like abducting the thigh). The anteversion angle refers to the angle of the central axis of the prosthetic acetabular cup relative to a plane parallel to the coronal plane, anterior to the coronal plane, so that opening of the cup is turned forward. This corresponds roughly to anteversion of the leg (twisting the leg from a duck toed to a pigeon toed position). The angle of this forward twist is the anteversion angle. The preferred angles are known as Lewinnek's Safe Zone. The "safe zone" defined by Lewinnek spans an inclination of 40°±10° and anteversion of 15°±10°.

Current methods of acetabular cup placement in total hip arthroplasty are labor-intensive and disregard the orientation of the neck (anteversion and offset). Currently, the desired placement of the prosthetic acetabular cup (the abduction angle and anteversion angle) are determined pre-operatively, using various combinations of pre-operative CT scans, X-Rays and pre-operative calculations. The actual placement is typically accomplished by hand, with the surgeon matching the actual placement to a predetermined placement (determined prior to the surgery).

SUMMARY

The system and methods described below provide placement of both the prosthetic acetabular cup and the prosthetic femoral head which takes account of the patient's particular anatomy, with inter-operative testing of the patient's body to find an optimum positioning (angles) for the components. The procedure may be accomplished with less pre-operative and inter-operative imaging, providing for reduced radiation exposure for doctors and patients. The method is useful even if the patient shifts position during the surgery, and does not require extensive registration steps to fix the pelvis position relative to the operating table or surgical equipment.

The system comprises a manipulable jig which can be fixed to the pelvis during surgery and test components. The jig is configured to hold test components including test versions of the prosthetic acetabular cup, the prosthetic femoral ball stem, and is manipulable, in conjunction with manipulations of the patient's hip and bad-hip leg (the leg on the side with the hip to be replaced), to test various angles of the prosthetic acetabular cup.

DETAILED DESCRIPTION OF THE INVENTIONS

Figure 1:
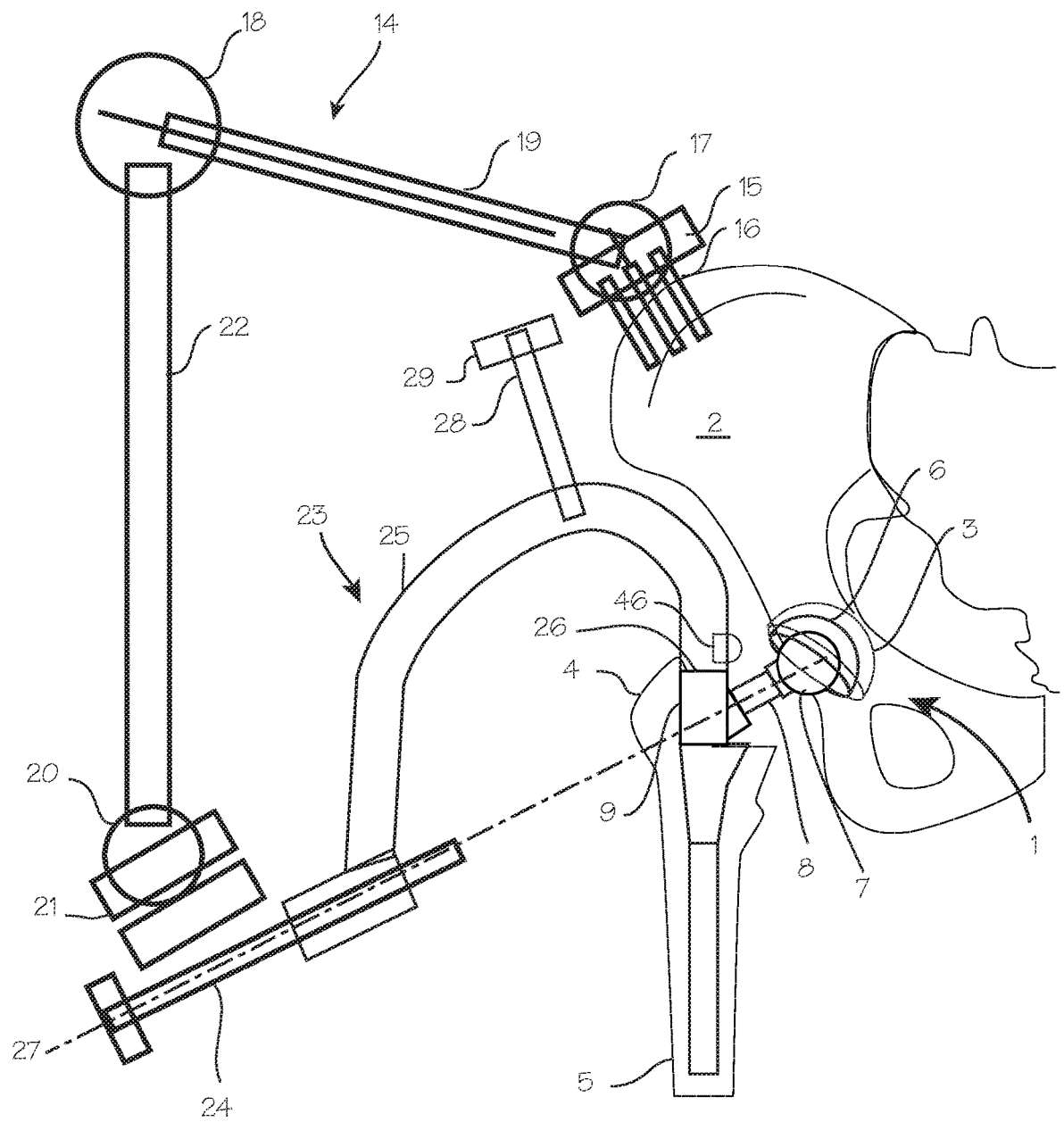
FIG. 1 illustrates a system for aligning a prosthetic acetabular cup in the acetabulum (hip socket) of a patient to accomplish total hip arthroscopy.

FIG. 1 illustrates a system for aligning a prosthetic acetabular cup in the acetabulum (hip socket) of a patient. The goal of the procedure is to replace natural components of the hip joint 1, including the pelvis 2 and the surface of the acetabulum 3 (the concave surface of the hip socket), and the femoral head 4 of the femur 5. The system is shown in a first configuration in FIG. 1. This configuration includes components needed for pre-installation testing of placements for a prosthetic acetabular cup and prosthetic femoral head, and includes a trial cup 6, a trial head 7, trial neck 8 and trial stem 9. Each of these components correspond to permanent components, specifically the prosthetic acetabular cup 10 (FIG. 6), prosthetic femoral head 11, prosthetic femoral neck 12 and prosthetic stem 13 (each shown in later figures). The trial stem 9 is configured for temporary non-translating fixation within the femur (that is, once fixed, though temporary, the trial stem does not rotate or translate relative to the femur). The system includes the jig 14. Generally, a jig is a device for accurately guiding and positioning a tool in relation to a workpiece, or for positioning the parts of an object during assembly. In this case the jig is a device for accurately guiding and positioning the prosthetic components in relation to the pelvis (the workpiece). The jig includes a fixation element 15 with a pin or screw (or several) 16. A first rotatable and lockable joint 17 is fixed to the fixation element. A second rotatable and lockable joint 18 is connected to the first rotatable and lockable joint 17 and fixation element through a first rod 19, and the second rotatable and lockable joint 18 is connected to a third rotatable and lockable joint 20 and aiming clamp 21 through a second rod 22. The aiming clamp 21 is releasably attachable to the handle assembly 23 and an alignment shaft 24 which is fixed within a handle portion 25. The handle is configured to hold the trial stem, trial neck, and trial head through a releasable connection 26. The trial cup 6 is configured to fit within the reamed acetabulum 3, and rotatable and reorientatable (glidable) within the acetabulum by impact of the trial head or trial skirt during manipulations described below. The fixation element is configured for temporary non-translating fixation to the pelvis (that is, once fixed, though temporary, the fixation element does not rotate or translate relative to the pelvis). The aiming clamp is configured for temporary non-translating fixation to the alignment shaft 24, not allowing deviation of the alignment shaft from the axis of the clamp. The releasable coupling 26 may be rotationally and longitudinally fixed to the trial stem, and readily disconnected from the trial stem. The alignment shaft is translatable within the handle, along the neck axis 27. The handle is configured to hold the alignment shaft 24 and the trial neck 8 on neck axis 27. A first strike rod 28 with a strike plate 29 may be removably attached to the handle, and when affixed to the handle the strike plate may be impacted with a mallet to adjust and manipulate the trial stem and ball in the fitting and alignment procedure (and prosthetic trial stem and ball). The rotatable and lockable joint 18 may comprise a lockable ball head assembly. A similar shape-lockable tube may be used in place of the entire chain of rotatable and lockable joint 18 and connecting rods, the rotatable and lockable joint(s) may comprise a shape-lockable tube, which may be bent and twisted as desired, and rigidly locked in a wide range of shapes, or other flexible mechanical arm fixable in a predetermined orientation. One or more of the rotatable and lockable joints may be omitted, if the remaining rotatable and lockable joints have sufficient range of motion to accommodate the manipulations described below. These means, and other comparable means for connecting the fixation element to the trial components, allowing manipulation of the trial components relative to the fixation element and trial cup and thereafter rigidly locking the jig in a shape after manipulation to rigidly fix the alignment shaft in alignment with the neck axis may be used as described below.

As shown in FIG. 1, the trial cup 6 is shown temporarily installed (not fixed within) in the acetabulum about a 45° abduction (tilt) angle. The anteversion (that is, the opening of the cup is facing directly laterally, relative to the patient, and not yet turned anteriorly, toward the front of the patient) is just a few degrees. At this point in the procedure, these angles are immaterial: the cup is just sitting in the reamed socket, awaiting alignment and fixation. The acetabulum 3 has been reamed, to create a concave pocket matching the outer convex surface of the trial cup 6.

Figure 2:
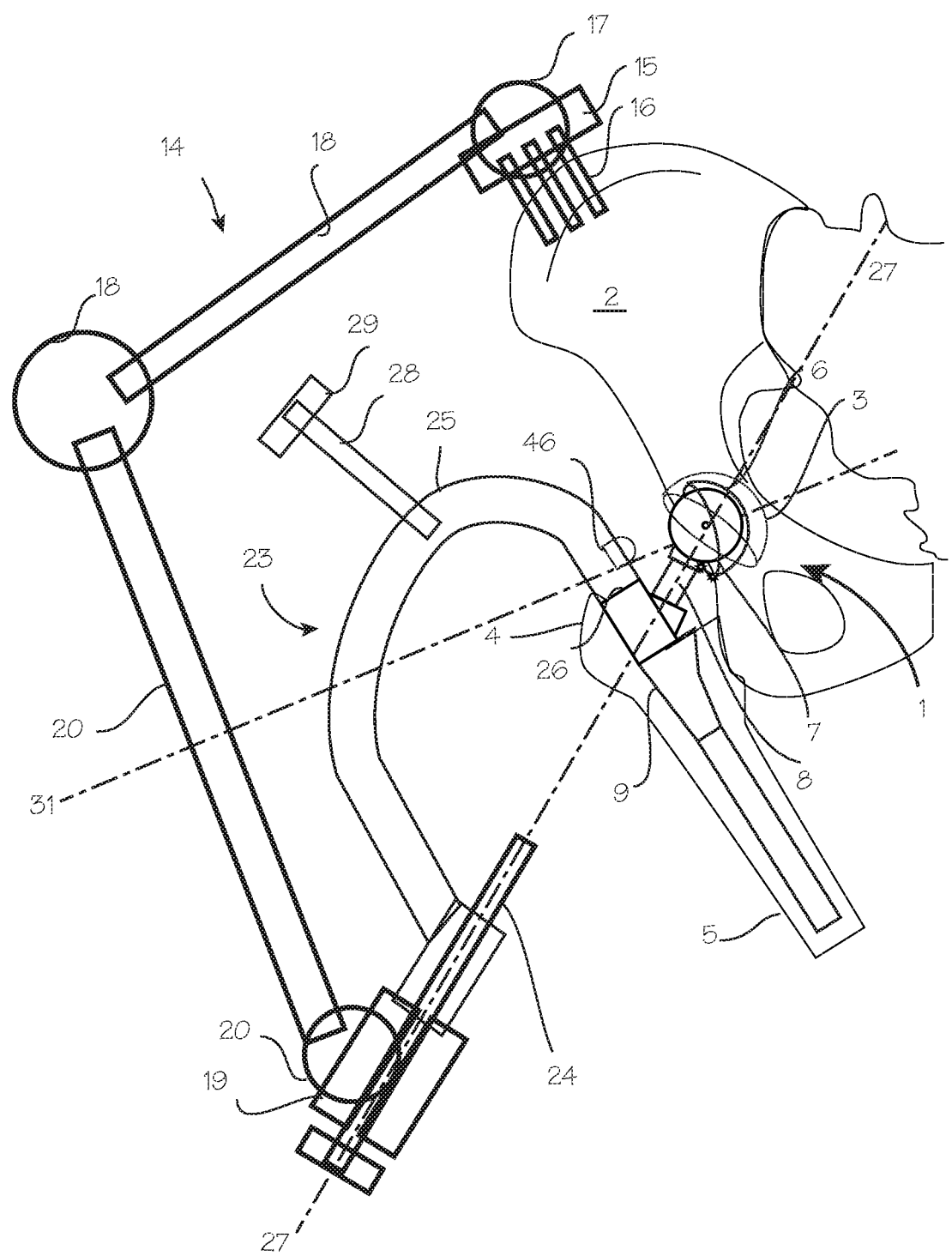
FIG. 2 illustrates the system of FIG. 1, after manipulations intended to determine a desired prosthetic acetabular cup position.
Figure 3:
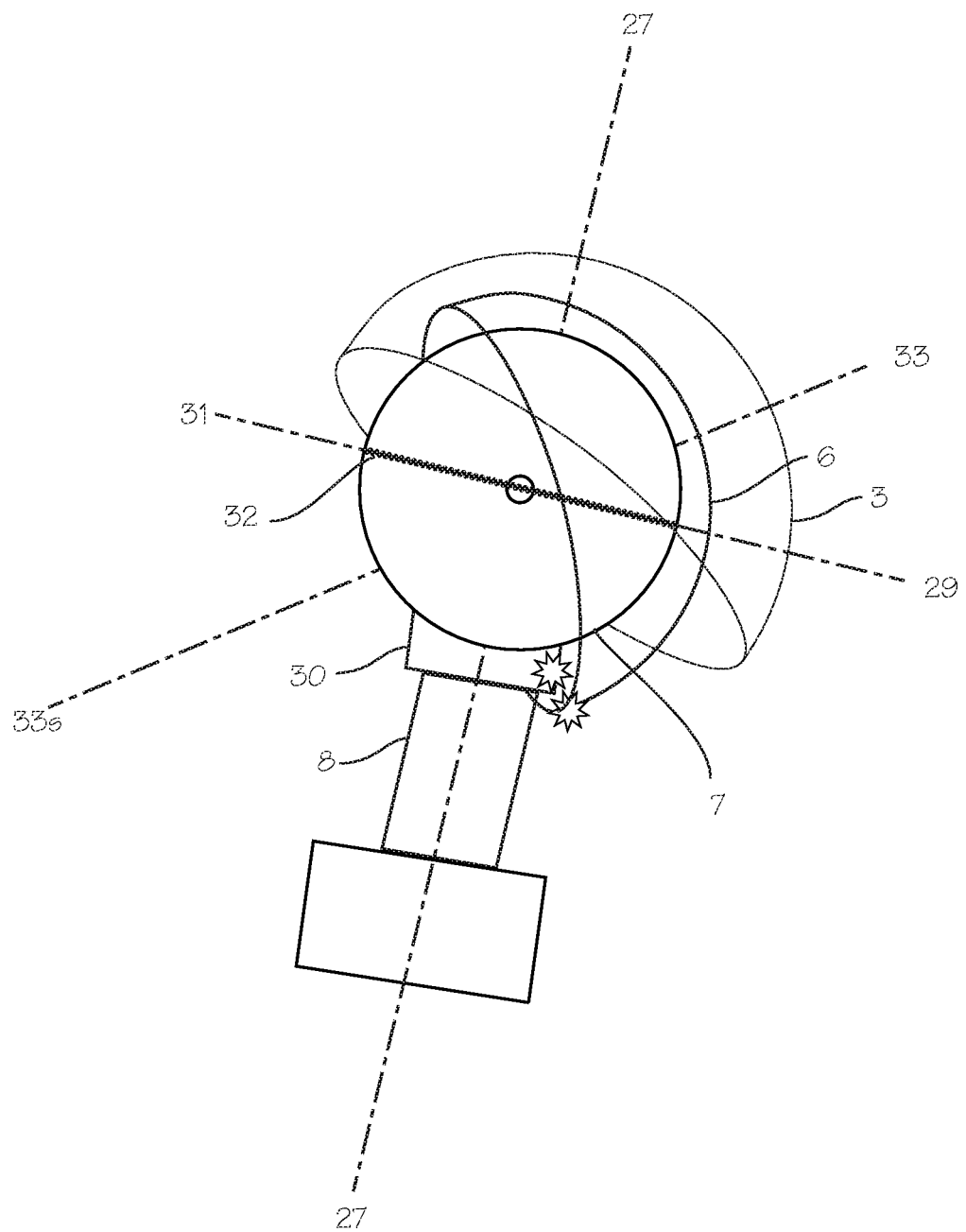
FIG. 3 is a close-up of the trial components, after manipulations intended to determine a desired prosthetic acetabular cup position.

FIG. 2 illustrates the system of FIG. 1, after manipulations intended to determine a desired prosthetic acetabular cup position. In this Figure, the patient's femur has been manipulated by the surgeon, and the trial head 7 and trial neck 8 are depicted at a position achieved during the manipulations. The manipulations may entail lifting the patient's thigh and femur to a tucked position, to move the trial cup to an abduction angle most suitable for the patient. Along with manipulation of the patient's thigh and femur, the manipulable jig components are manipulated to follow, as the jig is fixed to the femur via the trial stem and releasable coupling 26. Manipulation of the thigh and femur, and the test components results in impingement of the trial head or skirt on the rim of the trial cup, (*,* in the Figure). Upon manipulation to the furthest extent permitted by the patient's anatomy, and the position of the trial cup in the acetabulum (hip socket) 3 arrives, as pushed and rotated by the trial head or skirt, at the desired abduction (tilt) angle. At this point, the surgeon may operate the rotatable and lockable joint(s), such as the first rotatable and lockable joint 17, second rotatable and lockable joint 18 and third rotatable and lockable joint 20 of the fixation element and operate the aiming clamp 21 to lock the rotational position of the aiming clamp 21, which is already locked in a longitudinal position on the alignment shaft 24. However, further adjustments may be made with further manipulation, such as anteversion adjustments guided by internal rotation of femur and thigh to determine a suitable anteversion angle. FIG. 3 provides a close up view of the trial ball, trial neck, and trial cup, to more clearly show that the manipulation of the trial ball, trial neck (via manipulations of the femur and thigh) are accomplished such that the trial head (or the trial head skirt 30) may impact the rim of the trial cup, and push it into different orientations within the reamed acetabulum, if the trial reductions result in such impacts. FIG. 3 also shows the ball equator 31, and a marking 32 on the trial head ball equator (a "Ranawat line") mentioned below.

Figure 4:
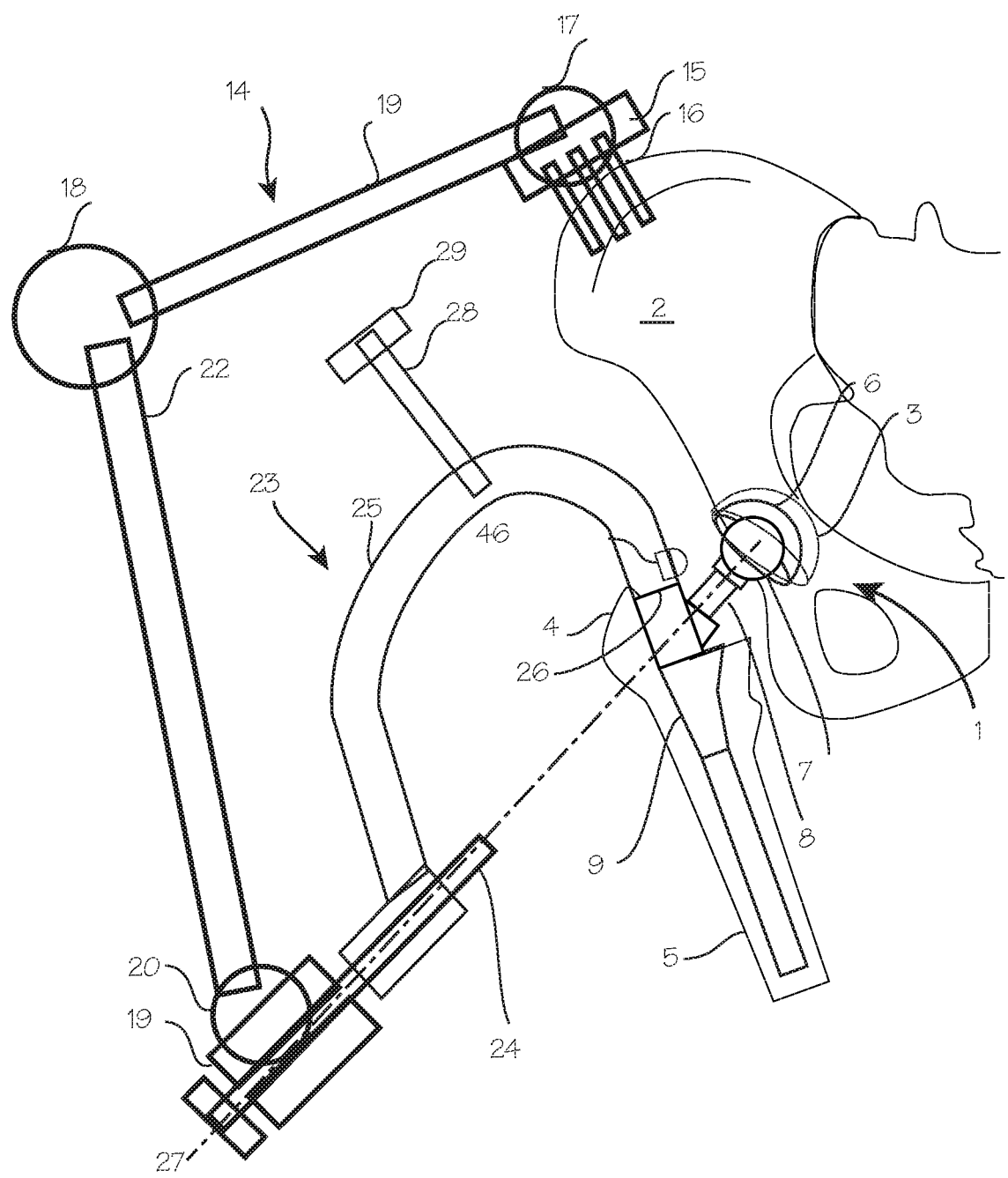
FIG. 4 illustrates the system of FIGS. 1 and 2, after manipulations to align the jig and trial components with the trial cup axis.

FIG. 4 illustrates the system of FIGS. 1 and 2, after manipulations to align the jig and trial components with the trial cup axis 33 (which, as describe below, is, in the orientation achieved at this point, the desired prosthetic acetabular cup axis). In this Figure, the patient's femur has been manipulated by the surgeon, and trial cup 6, the trial head 7 and trial neck 8 are depicted at a position which the surgeon has determined is best for the particular patient, after the manipulations discussed below. The manipulations at this step entail lifting the patient's thigh and femur to a position which also achieves the alignment of the neck axis with the cup axis (a reduction of sorts). Along with manipulation of the patient's thigh and femur and trial components, the manipulable jig components are manipulated to follow, as the jig is fixed to the femur via the trial stem and releasable coupling 26. After manipulations at this step, neck axis 27 (dashed line) is perpendicular to the plane established by the rim of the trial cup (the trial cup and prosthetic acetabular cup are spherical sections, so the rim lies within a plane). Once the surgeon has manipulated the jig and trial components to position the trial cup in the acetabulum (hip socket) 3 at the desired abduction (tilt) angle, the surgeon may operate the rotatable and lockable joint(s) and operate the aiming clamp 21 to lock the rotational position of the aiming clamp and lock the aiming clamp 21, which is already locked in a longitudinal position on the alignment shaft 24.

Figure 5:
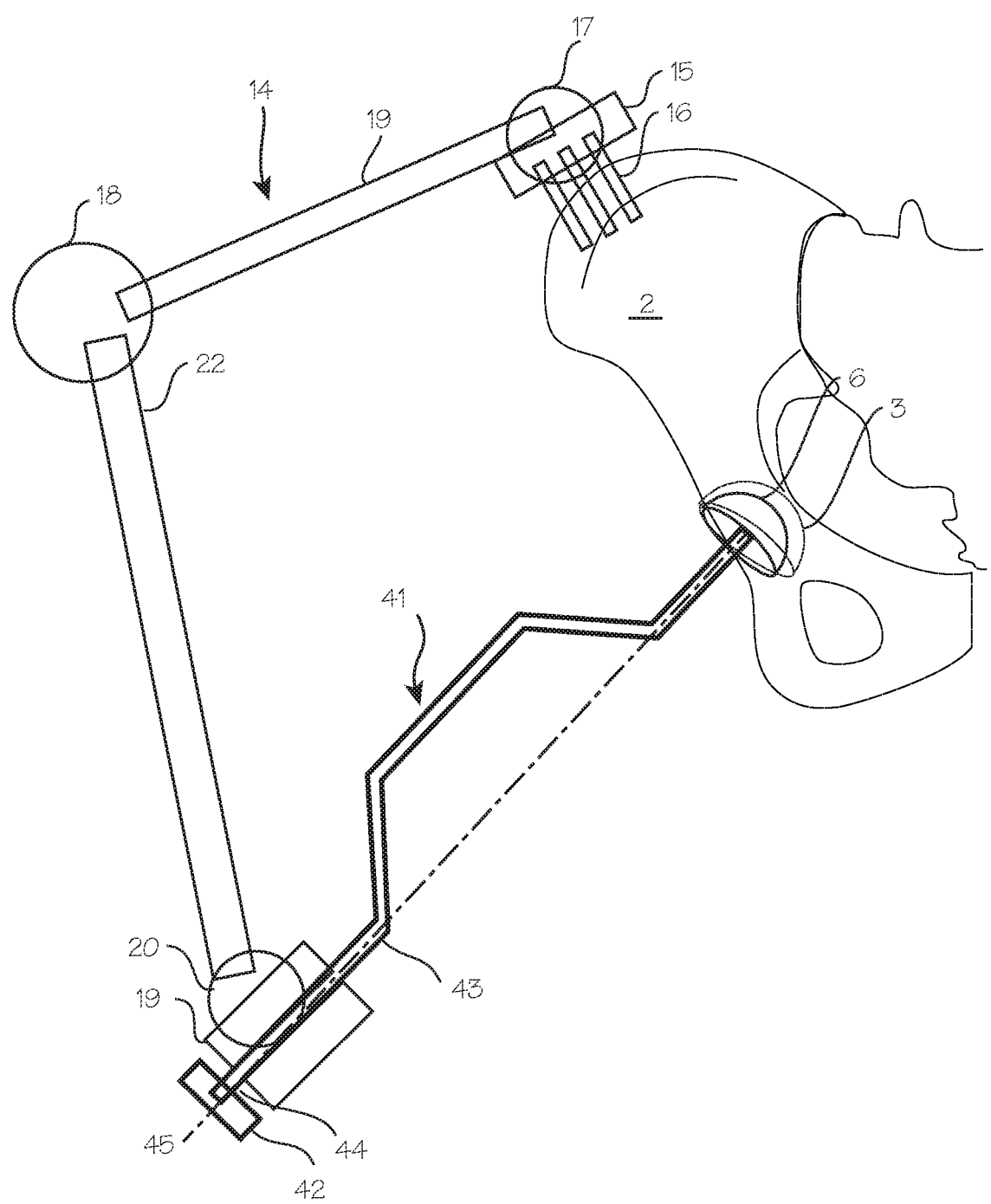
FIG. 5 illustrates a second configuration of the system, with components for permanently installing the prosthetic acetabular cup in the position determined using a trial cup, including an inserter fitted within the jig of the previous figures.

FIG. 5 illustrates a second configuration of the system, with components for permanently installing the prosthetic acetabular cup in the position determined using a trial cup, including an inserter fitted within the jig of the previous figures. This configuration retains the jig components including the fixation element 15 and the pin or screw (or several) 16, the rotatable and lockable joint 17, rotatable and lockable joint 18 connected to the fixation element through the first rod 19, and the third rotatable and lockable joint 20 connected to an aiming clamp 22 through the second rod 22. In this configuration, the handle and alignment shaft 24 are removed from the system, and the trial components are set aside, and the handle may be disconnected from the trial stem at the releasable attachment mechanism 26. An acetabular cup inserter 41 with a strike plate 42 (at the proximal end of the cup inserter) and an inserter rod 43

(preferably an offset inserter rod) is shown installed within the aiming clamp 21. The cup inserter grasping bar 44 (the proximal end of the inserter rod) of the cup impactor rod are slidably engaged within the aiming clamp 21, though fixed within the clamp such that the inserter axis 45 cannot deviate from the clamp axis, which, referring to FIGS. 1 and 2, cannot deviate from the neck axis 27 and long axis of the alignment shaft 24 and the intended axis of the prosthetic acetabular cup 10. The end of the impactor bar opposite the strike plate 42 is configured to (temporarily) accept and hold the prosthetic acetabular cup 10, with the cup axis and cup rim of prosthetic acetabular cup oriented along the same line as the trial cup axis and trial cup rim of trial cup 6 established in FIGS. 2 and 4. The strike plate 42 is configured to be struck by a mallet, and the inserter rod is configured to transmit force applied by the mallet to the prosthetic acetabular cup 10, to drive the cup into the acetabulum. After this step, the fixation element may be removed, the implantable prosthetic femoral head 11, prosthetic femoral neck 12 and prosthetic stem 13 may be permanently installed in the patient's femur, and the femur and thigh may be put back in place with the implantable prosthetic femoral head 11 seated in the prosthetic acetabular cup 10.

Figure 6:
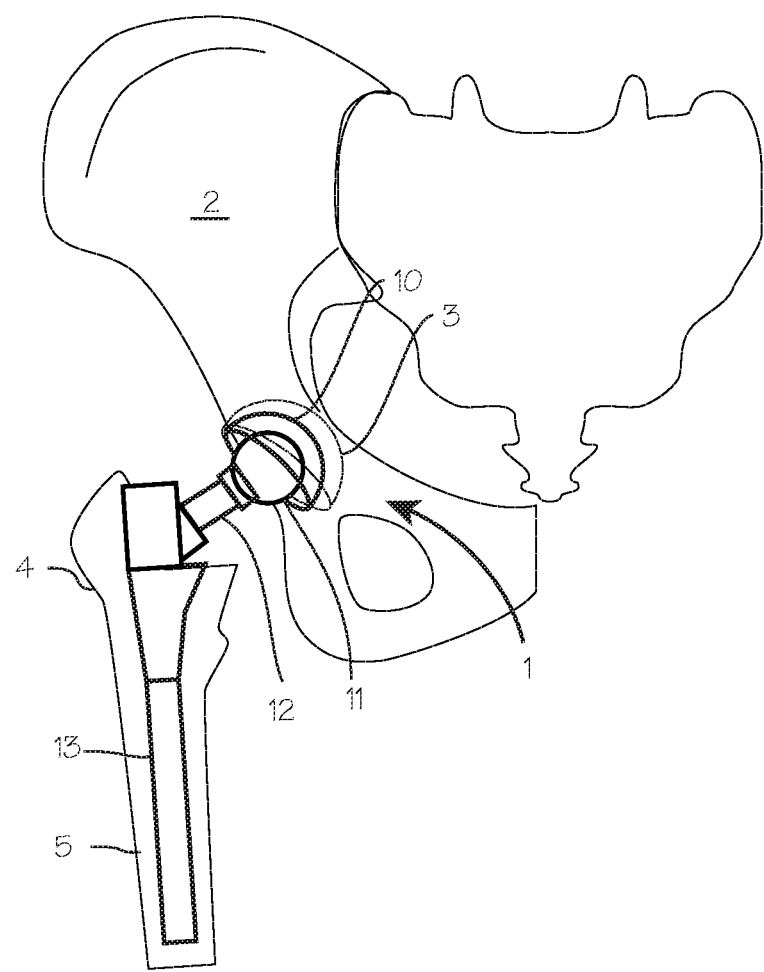
FIG. 6 illustrates replacement of the patient's femur after implantation of the prosthetic acetabular cup, with the implantable head, neck and stem permanently installed in the femur, and the femur in a neutral position.

FIG. 6 illustrates re-placement (reduction) of the patient's femur after implantation of the prosthetic acetabular cup 10, with the implantable head 11, neck 12, neck and stem 13 permanently installed in the femur 5, and the femur in a neutral position (for example, a natural oblique position or other favored final position) and with the implantable head 11 disposed within the prosthetic acetabular cup 10. The prosthetic acetabular cup 10 is shown at an abduction angle of about 45°, and a slight anteversion angle of about 10°.

The method of using the system includes various steps to temporarily lock the jig to the patient's pelvis, temporarily lock the trial jig to the trial stem, trial head and trial cup, and temporarily fix the trial stem, trial head and trial cup to the patient's femur, manipulating the patient's hip and thigh with the jig and trial components temporarily attached, determine a desired final position of the prosthetic acetabular cup, and operating the rotatable and lockable joint(s) to lock the jig in the position in which it achieves upon positioning the prosthetic acetabular cup in the desired final position.

A first trial "reduction" (putting the joint and trial components back where they belong) and manipulation may then be performed, in which the surgeon flexes the patient's hip and bad-hip leg, preferably to about 100°, internally rotates the femur to about 50°, and causing/allowing the trial neck (and the skirt of the trial head, if the trial head (and real head) are skirted) to impinge on the rim of the trial cup 6, thereby forcing and twisting the trial cup to an orientation in which the cup axis (which coincides with the neck axis and alignment shaft axis) is pointed in a direction which is considered by the surgeon to be an optimum for the patient (typically, the safe zone known to prevent posterior dislocation, and a more stable position). The trial neck and/or skirt is sized to impinge on the rim of the trial cup, and not on the pelvis surrounding the trial cup, to force the trial cup to rotate within the reamed acetabulum to the stable position. At this point, if the trial cup has been moved to a position where osteophytes (bone growths) protrude above the trial cup rim, the surgeon may at this point remove them.

A second trial reduction and manipulation may then be performed, in which the surgeon extends the bad-hip leg fully in the hip and knee and internally rotates the foot to the maximum extent (between a pigeon toe position and a duck toe position). This may result in impingement (unless the trial cup is already in a desirable orientation and stable position) of the trial cup on the posterior edge of the reamed acetabulum (for external rotation), which results in pushing the acetabular trial cup into less anteversion to prevent possible anterior dislocation, or this may result in impingement (unless the trial cup is already in a desirable orientation) of the trial cup on the anterior edge of the reamed acetabulum (for internal rotation), which results in pushing the acetabular trial cup into more anteversion to prevent possible posterior dislocation. (If, as a result of this manipulation, the trial cup is re-oriented within the reamed acetabulum so that osteophytes protrude beyond the posterior portion of the rim of the trial cup, the surgeon may need to remove them). This duck toe/pigeon toe manipulation may be repeated as necessary to ensure that the trial cup is forced into a desired anteversion angle. The optimal orientation of the trial cup is thereby established.

After the surgeon determines the desired trial cup orientation, the surgeon will lock the jig in the shape corresponding to the desired trial cup orientation achieved by the manipulation. This is done by further manipulating the bad-hip leg and correspondingly manipulating the affixed handle 25 to align the equator of the trial head with the rim of the trial cup (in a parallel plane, relative to the plane of the rim), and therefore perpendicular to the trial cup axis, which may be a Ranawat line, and which may be on the equator of the ball, perpendicular to the stem axis (the Ranawat line may be etched on the equator or a parallel latitude line of the ball), and thus the axis of the trial head and neck will be aligned with the axis of the trial cup, and the axis of the alignment shaft 24 will be in line with the trial cup axis. This shape of the jig is preserved by locking the aiming clamp around the alignment shaft 24 and locking the rotatable and lockable joint(s). (Rotation and manipulation of the handle necessitates rotation and manipulation of the femur and thigh, and vice-versa, because they are locked to the handle, indirectly, through the trial stem and releasable coupling).

With the jig shape, including the angles of the components such as the aiming clamp 21, the rotatable and lockable joint(s) and the two arms 19 and 22 corresponding to desired cup placement determined, and thus angle of the alignment shaft 24 which corresponds to the desired cup placement, thus determined, the shape is fixed by tightening the rotatable and lockable joint(s) or otherwise locking the jig. Preferably, this shape corresponds to an orientation of the trial cup in a dynamically safe zone, but the shape may correspond more generally to a desired orientation as determined by the surgeon, or as calculated using computer guided surgery systems.

With the jig set in the fixed configuration, with the rotatable and lockable joint(s) locked to preserve the jig shape, the surgeon may remove the alignment shaft 24 from the handle, and the handle, trial stem, trial neck and trial head and trial cup are all removed from the surgical field and set aside. (The surgeon may have to move the femur out of the way.) The jig remains rigidly fixed to the pelvis via the pins 16, but is no longer fixed to the femur. The surgeon then installs the prosthetic acetabular cup into the acetabulum by setting it on the distal end of the inserter 43, setting the inserter bar 44 within the aiming clamp 21, thereby placing the inserter slidably within the clamp, fixed along the cup axis but translatable along the axis, and translating the inserter and attached prosthetic acetabular cup toward the reamed acetabulum. With the jig components including the fixation element 15, rotatable and lockable joint(s), aiming clamp 21 holding the inserter 43 by the inserter bar 44, the surgeon may strike the inserter strike plate 42 to drive the prosthetic acetabular cup 10 into the reamed acetabulum.

Along with seating the prosthetic acetabular cup 10 securely within the reamed acetabulum, the surgeon will permanently secure the prosthetic head 11, prosthetic neck 12 and prosthetic stem 13, and replace the patient's femur so that the prosthetic head 11 seats in the prosthetic acetabular cup 10, to finish the installation.

The jaws of the aiming clamp have an interior contour keyed to the cross-sectional shape of both the bar 44 and the alignment shaft 24, such that translation of the bar or shaft along the neck axis 27 may be permitted, without allowing the longitudinal axis of the bar or shaft (or that portion gripped by the clamp) to deviate from neck axis 27.

A camera 46 may be disposed on the handle, proximate the releasable attachment mechanism and trial stem and ball, and is aimed at the ball (the trial ball or the permanent ball) to provide a view of the ball and cup during fitting and installation, so that the procedure may be accomplished with minimal surgical opening of the hip. In a more open procedure, the surgeon may directly view the joint, without the aid of the camera.

The jig may be indexed, with markings enabling recording of indices, so that it may be loosened, the test components removed, and final implantable components installed on the jig, and the jig may be returned to the indexed configuration to replicate the favored position determined in testing steps.

The fixation element may be fixed to the operating table, rather than the pelvis as shown, if the patient may be securely fixed to the table as well, such that the hip and fixation element will not move relative to each other during the procedure, including the large manipulations necessary for the procedure.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A system for aligning a prosthetic acetabular cup in a pelvis of a patient, said system comprising:
   a trial cup, configured to fit into a reamed acetabulum in the pelvis of the patient;
   a trial femoral head, trial neck and trial stem, said trial neck having a long axis;
   a jig comprising a fixation element connected to a first rotatable and lockable joint, a first connecting rod connecting said first rotatable and lockable joint to a second rotatable and lockable joint, a second connecting rod connecting said second rotatable and lockable joint to a third rotatable and lockable joint and an aiming clamp;
   a handle assembly comprising a handle portion characterized by a proximal end and a distal end, and an alignment shaft disposed on the proximal end of the handle portion, and a releasable coupling on the distal end, said releasable coupling configured for releasably coupling to the trial stem;
   said alignment shaft characterized by a long axis, said handle portion configured to hold said alignment shaft with the long axis of the alignment shaft coaxial with a long axis of the trial neck;
   wherein the fixation element is configured for temporary non-translating fixation to the pelvis;
   the aiming clamp is configured for temporary fixation to the alignment shaft;
   wherein the trial stem is configured for temporary non-translating fixation within a femur of the patient; and
   wherein the first rotatable and lockable joint, the second rotatable and lockable joint, and the third rotatable and lockable joint and aiming clamp, are operable to be manipulated, upon manipulation of the femur, to a position corresponding to a desired orientation of the trial cup and the prosthetic acetabular cup, and operable to be fixed in a fixed position, said fixed position being a position corresponding to a desired orientation of the trial cup and the prosthetic acetabular cup.

2. The system of claim 1, wherein the trial cup is configured to fit within the reamed acetabulum, and be rotatable within the acetabulum by impact of the trial head or trial skirt.

3. The system of claim 1, wherein a trial femoral head and/or the trial neck are configured to impact on a rim of the trial cup upon manipulation of the jig, to force the trial cup to rotate within the reamed acetabulum.

4. The system of claim 1 wherein the first rotatable and lockable joint, the second rotatable and lockable joint, and the third rotatable and lockable joint are further operable to be released from the fixed position, and thereafter returned to the fixed position.

5. The system of claim 1, wherein one or more of the first rotatable and lockable joint, the second rotatable and lockable joint, and the third rotatable and lockable joint comprise a lockable ball head.

6. The system of claim 1, wherein each of the first rotatable and lockable joint, the second rotatable and lockable joint, and the third rotatable and lockable joint comprise lockable ball mounts.

7. The system of claim 1, further comprising a camera disposed on the distal end of the handle assembly, said camera configured to obtain images of the trial head and trial cup when the handle assembly is fixed to the trial stem and the trial stem is fixed to the femur.

8. The system of claim 1, further comprising an inserter, said inserter characterized by an inserter axis, and having a proximal end and a distal end, with an inserter grasping bar disposed on said proximal end, wherein the inserter grasping bar is configured to be grasped by the aiming clamp and fixed within the clamp such that the inserter axis cannot deviate from the clamp axis and long axis of the trial neck, said inserter distal end configured for releasable attachment to the prosthetic acetabular cup.

9. The system of claim 1 further comprising a camera disposed on the handle assembly said camera configured to obtain images of the trial cup and trial head when the head is disposed within the trial cup.

10. The system of claim 1 wherein the alignment shaft is removable from the handle assembly.

11. A system for aligning and installing a prosthetic acetabular cup in a pelvis of a patient, said system comprising:
   a trial cup, configured to fit into a reamed acetabulum in the pelvis of the patient, said trial cup configured for rotation within the reamed acetabulum;

trial components including a trial femoral head, trial neck and trial stem, said trial neck having a trial neck long axis;

a jig comprising a fixation element and an aiming clamp;

handle means for releasably connecting the aiming clamp to the trial components, said handle means comprising an alignment shaft configured for releasable fixation to the aiming clamp;

said jig further comprising means for connecting the fixation element to the aiming clamp, with the aiming clamp fixed to the trial components through alignment shaft of the handle means, allowing manipulation of the trial components relative to the fixation element and trial cup and thereafter rigidly locking the jig in a shape after manipulation to rigidly fix the alignment shaft in alignment with the trial neck long axis; and an inserter characterized by an inserter axis, said inserter configured for fixation within the aiming clamp, such that inserter is rigidly fixed within the alignment clamp with the inserter axis aligned with the trial neck longitudinal axis, such that, upon removal of the alignment shaft from the aiming clamp, the inserter may be fixed to the aiming clamp such that the inserter axis is aligned on trial neck longitudinal axis.

12. A method of performing total hip arthroplasty on a pelvis and femur of a patient, said method comprising:

installing a trial cup in a reamed acetabulum in the pelvis of the patient, such that said trial cup is rotatable within the reamed acetabulum;

temporarily installing trial components including a trial head and trial neck in the femur;

manipulating the femur with the installed trial components through a range of movement, with the trial head disposed within the trial cup, as necessary to impact a rim of the trial cup with the trial head and rotate the trial cup within the reamed acetabulum and position the trial cup in a stable position;

temporarily securing the trial stem to a handle means, and temporarily securing the handle means to a manipulable and lockable jig, and temporarily securing the manipulable and lockable jig to the pelvis;

after the step of manipulating the femur to position the trial cup in a stable position, further manipulating the femur to place the femur and trial components in a position in which an axis of the trial head and neck coincides with an axis of the trial cup, and thereafter locking the manipulable and lockable jig into the shape corresponding to the position in which an axis of the trial head and neck coincides with an axis of the trial cup;

disconnecting the handle means from the trial components and the jig; and temporarily securing to the jig an inserter with an implantable acetabular cup attached, with an axis of the inserter aligned with the axis of trial cup determined in the locking step, locating the implantable acetabular cup in the reamed acetabulum, and thereafter operating the inserter permanently secure the implantable acetabular cup in the reamed acetabulum.

13. The method of claim 12, further including the steps of:

replacing the trial components with permanently implantable femoral head, neck and stem; and assembling the femur and hip with the permanently implantable femoral head disposed within the implantable acetabular cup.

* * * * *